United States Patent [19]

Sugiura et al.

[11] Patent Number: 5,846,593
[45] Date of Patent: Dec. 8, 1998

[54] FOOD MATERIALS CONTAINING SESAMINOL TRIGLUCOSIDE DERIVED FROM SESAME SEEDS

[75] Inventors: Masato Sugiura; Masanori Inayoshi; Shigeo Sakurai, all of Aichi; Kenichi Iguchi, Osaka; Toshihiko Osawa, Aichi, all of Japan

[73] Assignees: Takemoto Yushi Kabushiki Kaisha, Aichi; Corunum Corporation, Tokyo, both of Japan

[21] Appl. No.: 724,368

[22] Filed: Oct. 1, 1996

[30] Foreign Application Priority Data

Oct. 2, 1995 [JP] Japan .................................. 7-279697

[51] Int. Cl.$^6$ ...................................................... A23L 1/20
[52] U.S. Cl. ............................................. 426/629; 426/430
[58] Field of Search ..................................... 426/629, 430, 426/425

[56] References Cited

U.S. PATENT DOCUMENTS 3,993,535  11/1976  Karnofsky .............................. 426/430
5,606,035  2/1997  Kawakishi et al. .

*Primary Examiner*—Anthony J. Weier
*Attorney, Agent, or Firm*—Keiichi Nishimura

[57] ABSTRACT

A food material containing sesaminol triglucoside by at least 3.0 mm per 1 g of its dry component is obtained by subjecting dehulled sesame seeds to an extraction process at an extraction temperature below 120° C. with aliphatic hydrocarbon as extraction solvent to obtain a solution, removing the solution to obtain a solid which contains the extraction solvent by less than 10 weight %, adding water to this solid to obtain a water-containing object, and removing the residual solvent from this water-containing object by distillation at 20–120° C. The food material thus obtained is substantially free of the solvent used in the extraction process and has improved color, flavor and taste.

4 Claims, No Drawings

FOOD MATERIALS CONTAINING SESAMINOL TRIGLUCOSIDE DERIVED FROM SESAME SEEDS

BACKGROUND OF THE INVENTION

This invention relates to food materials containing sesaminol triglucoside derived from sesame seeds, and more particulary to a method of producing such food materials.

Many products obtained from sesame seeds are widely appreciated as tasteful food material. Recently, these products are appreciated also as functional foods because sesame seeds contain not only oil-soluble lignans such as sesamin, sesaminol and sesamolinol as physiologically active substances, but also water-soluble lignan glucosides such as pinoresinol glucosides and sesaminol glucosides. An object of this invention is to provide new food materials containing at high concentration sesaminol triglucoside which is a water-soluble lignan glucoside derived from sesame seeds.

Known examples of products obtained by processing sesame seeds include roasted sesame seeds obtained by roasting sesame seeds, ground sesame seeds obtained by grinding roasted sesame seeds and sesame pastes obtained by grinding finely and kneading roasted sesame seeds. These processed sesame seed products contain fats by about 50% by weight, however, and hence are high-calorie food products. When sesame seeds are roasted, furthermore, aforementioned water-soluble lignan glucosides are nearly completely decomposed and hence their content is extremely low.

On the other hand, a large amount of sesame seeds is being used for the production of sesame seed oil, which is obtained mostly by compressing sesame seeds by a machine. Sesame seed oil, however, does not contain water-soluble lignan glucosides by its own nature. Although so-called sesame meal is obtained as compression residue when sesame seed oil is obtained by compression as described above, the content of water-soluble lignan glucosides in sesame meal is also extremely low because they are decomposed almost completely by the heat generated during the compression process for obtaining sesame seed oil. Moreover, sesame meal is dark-colored due to decomposition products of proteins and waste fatty acids, and since it has strange taste and odor, it is not suited to serve as a food material. The fact is that sesame meal is currently being used only as animal feed or fertilizer.

There are known methods of separating water-soluble lignan glucosides from sesame seeds (for example, Japanese Patent Publications Tokkai 6-116282 and 6-306093). These methods involve very troublesome operations and the yield of water-soluble lignan glucosides is low.

SUMMARY OF THE INVENTION

The problem to be solved by this invention was that prior art sesame seed products had only a very low content of physiologically active water-soluble lignan glucosides, and more particularly of sesaminol triglucoside, and that they could not easily be presented as a food material because of their color, flavor and taste.

In view of the above, the inventors herein worked diligently to discover a new food material having a high concentration of sesaminol triglucoside derived from sesame seeds and superior color, flavor and taste as a food material. As a result, it was discovered that the above and other objects can be accomplished if dehulled sesame seeds are subjected to a series of specified processes including a first process of using aliphatic hydrocarbon as extraction solvent to subject dehulled sesame seeds to an extraction process at a temperature below 120° C. and removing the solution from the extract to obtain a solid containing this extraction solvent by less than 10 weight %, a second process of adding water to the solid obtained in the first process to obtain a water-containing substance, and a third process of distilling away the residual extraction solvent at +a temperature of 20–120° C. to obtain a food material which contains substantially no extraction solvent but contains sesaminol triglucoside at a rate of more than 3.0 mg per 1 g of the dry component.

DETAILED DESCRIPTION OF THE INVENTION

In the first process, dehulled sesame seeds are subjected to an extraction process at a temperature below 120° C. by using an aliphatic hydrocarbon as solvent for the extraction. The solution is removed from the extracted system and a solid containing this solvent for extraction by less than 10 weight % is obtained.

Sesame seeds which have been dehulled by any known method may be used as the dehulled sesame seeds in this process. Examples of such known method include the so-called mechanical dehulling method whereby sesame seeds are caused to rub against one another in the presence of water such that their hulls are removed and the so-called chemical dehulling method whereby an aqueous alkali solution is used to stir sesame seeds. It is preferable for the first process to use sesame seeds which have thus been dehulled and then dried. It is even more preferable to use such sesame seeds which have further been crushed for improving the efficiency of defatting the dehulled sesame seeds. In what follows, "dehulled sesame seeds" will include sesame seeds which have been dehulled, dehulled sesame seeds which have been dried, and dehulled and dried sesame seeds which have further been crushed.

In the first process, dehulled sesame seeds as described above are subjected to an extraction process by using a solvent. The solvent to be used is an aliphatic hydrocarbon such as butane, pentane, hexane and heptane, but hexane is favorable. A prior art extraction apparatus may be used such as batch type extractors, semi-continuous extractors and continuous counter-current system extractors.

The extraction is carried out at a temperature below 120° C., but a temperature range between room temperature and 80° C. is preferred. If the extraction temperature exceeds 120° C., the water-soluble sesaminol triglucoside in sesame seeds, and hence also in the dehulled sesame seeds, is decomposed suddenly.

After this extraction process with a solvent, the solution is removed from the extracted system to obtain a solid. A prior art method of removing the solution from a extracted system may be used, such as centrifugal separation, pressure-type filtration and low-pressure filtration. A distillation method under normal or reduced pressure may be used in combination. No matter which method is used for the removal of the solution, this is to be done at a temperature below 120° C. If so desired, the solution thus removed may be used for obtaining sesame seed oil therefrom.

It is important to reduce the solvent content of the solid thus obtained to less than 10% by weight in order to make it easier for the solid to absorb water in the second process, to be described below.

In the second process, water is added to the solid obtained in the first step and a water-containing object is obtained.

Water is normally added at a rate of 10–200 weight parts, but preferably 20–80 weight parts, for 100 weight parts of the solid obtained in the first process. A method of adding water with stirring or a method of spraying water with stirring may be used.

It is preferable to add ethyl alcohol, as well as water, in the second process. Ethyl alcohol is added at a rate of 50–200 weight parts, and preferably 75–150 weight parts, for 100 weight parts of water. If ethyl alcohol and water are to be used together, it is preferable to preliminary prepare an aqueous solution of ethyl alcohol at a specified concentration. It is also preferable to use buffer water of pH 7–9 in the second process. A known buffer water of this type can be used but the kinds of buffer water using potassium dihydrogen phosphate-sodium hydroxide or glycine-sodium chloride-sodium hydroxide are preferred from the point of view of safety for foods. If use is made of ethyl alcohol and water together, buffer water with pH 7–9 or a combination of ethyl alcohol and buffer water with pH 7–9, as explained above, it becomes possible in the third process to obtain a food material containing sesaminol triglucoside (which is a water-soluble lignan glucoside) at a higher concentration and having improved color, flavor and feeling in the mouth.

In the third process, the residual solvent is distilled away from the water-containing object obtained in the second process to obtain a food material which contains substantially no solvent used for the extraction process. Known method and apparatus may be used for this distillation process but this process must be carried out at a temperature below 120° C., and preferably at a temperature as low as possible and as quickly as possible.

In the third process, the water content of the food material is reduced normally to less than 10 weight % but preferably to less than 5 weight %. If the water content exceeds 10 weight %, and if it exceeds 12 weight % in particular, it tends to acquire an unpleasant taste, flavor and color due to putrefaction, depending on the storage conditions.

Known examples of water-soluble lignan glucosides contained in sesame seeds include (1) lignan polyglucosides of unknown structure with high-molecular glucose combined to hydroxyl group of the lignan molecule having sesaminol, sesamolinol or pinoresinol as aglucon (Japanese Patent Publication Tokkai 62-238287), (2) sesaminol monoglucoside and sesaminol diglucoside of known structures obtained by reacting β-glucosidase with these sesaminol polyglucosides (Japanese Patent Publication Tokkai 6-306093), and (3) pinoresinol triglucoside with known structure (Japanese Patent Publication Tokkai 6-116282). Food materials obtained in the third process contain more than 3 mg of sesaminol triglucoside (and normally at a rate of 3.0–6.0 mg) per 1 g of the dried component, containing substantially no other lignan glucosides of the type described above.

In summary, food materials, thus obtained through the aforementioned first, second and third processes, contain substantially no solvent used for the extraction, contain more than 3.0 mg of sesaminol triglucoside per 1 g of the dried component, and have superior color, flavor and taste. Thus, food materials according to this invention can serve both as ordinary foods and as functional foods. When they are to serve as functional foods, the materials obtained in the third process may be further processed into different shapes and particle sizes through crushing, classification and particle-forming steps.

The present invention may be practiced, for example, in any of the following five manners. By any of these methods, it is possible to obtain food materials containing substantially no solvent, containing more than 4.0 mg of sesaminol triglucoside per 1 g of dried component and having superior color, flavor and taste as food material.

According to Method (1), commercially available dehulled sesame seeds are rolled and flattened, and hexane is added for extraction at 50° C. for one hour. The solution is separated thereafter at room temperature by reduced pressure filtration to obtain a solid containing hexane by 1.5 weight % (the first process). Next, 40 weight parts of water are sprayed to 100 weight parts of this solid with stirring to obtain a water-containing object (the second process). Finally, the extraction solvent is distilled away from this water-containing object at 80° C. and under reduced pressure condition of 1 KPa to obtain a food material according to this invention.

Method (2) is similar to Method (1) except 72 weight parts of aqueous ethyl alcohol solution with weight ratio water/ethyl alcohol=100/80 are used instead of 40 weight parts of water used in Method (1).

Method (3) is similar to Method (1) except 88 weight parts of aqueous ethyl alcohol solution with weight ratio water/ethyl alcohol=100/120 are used instead of 40 weight parts of water used in Method (1).

Method (4) is similar to Method (1) except 40 weight parts of buffer water with pH 7.1 are used instead of 40 weight parts of water used in Method (1).

Method (5) is similar to Method (1) except 80 weight parts of aqueous solution of ethyl alcohol with weight ratio of buffer water with pH 8.8/ethyl alcohol=100/100 are used instead of 40 weight parts of water used in Method (1).

EXAMPLES

In what follows, the invention is described more in detail by way of test examples and comparison examples, but these examples are not intended to limit the scope of the invention. Unless otherwise noted, "parts" and "%" will mean "weight parts" and "weight %".

Part 1 (Examples wherein water is used in the second process)

Following sample food materials were prepared and tested.

Test Example 1

Commercially available sesame seeds were crushed by means of a flaking roll and 1 kg of sesame seeds thus crushed was placed inside a container with a stirrer, into which 1 liter of hexane was added. After it was stirred for one hour at 50° C., the content was separated at room temperature into a liquid and a solid by means of a suction filter (the first process). The content of the extraction solvent in this solid was 1.5%. Next, water 80 g was sprayed to 200 g of this solid and a water-containing object was obtained by stirring (the second process). Finally, 280 g of this water-containing objects were moved into a vacuum dryer to distill away the extraction solvent at a reduced pressure of 1 KPa at 80° C. for 5 hours to obtain 180 g of a food material (the third process).

Test Example 2

Another food material 194 g was obtained as in Test Example 1 except 280 g of the water-containing object were moved into a chamber dryer to distill away the extraction solvent at 80° C. for seven hours under a stationary condition.

Test Example 3

Still another food material 180 g was obtained as in Test Example 1 except 120 g, instead of 80 g, of water were used in the second process.

Test Example 4

Commercially available dehulled sesame seeds 1 kg were compressed by an expeller and their compressed residue (remaining fat components 30%) 1 kg was taken inside an autoclave with a stirrer. Hexane 1 liter was added and stirred for one hour at a pressure of 1 MPa and temperature of 100° C., and the content was separated into a solid and a liquid component by a centrifugal separation method at room temperature (the first process). The content of extraction solvent in this solid was 4.3%. Next, 180 g of water were sprayed on this solid 200 g and stirred to obtain a water-containing object (the second process). Finally 280 g of this water-containing object were placed inside a chamber dryer to remove the extraction solvent at 110° C. for four hours under a stationary condition to obtain 172 g of a food material.

Comparison Example 1

After the solid obtained in the first process of Test Example 1 was placed inside a vacuum dryer directly without being subjected to the second process, the extraction solvent was distilled away for 5 hours under a reduced pressure condition of 1 KPa and at a temperature of 80° C. Since 340 ppm of residual hexane were detected at this point, another distillation was carried out further under a normal pressure condition at 150° C. for 3 hours to obtain 177 g of a food material.

Comparison Example 2

A solid containing the extraction solvent by 20% was obtained as done in Test Example 1 except natural filtration was carried out instead of suction filtration in the first process. The second and third processes were carried out as in Test Example 1. Since residual hexane of 230 ppm was still detected after the distillation of extraction solvent was carried out for five hours under a reduced pressure condition of 1 KPa at 80° C., the distillation process was further resumed for three hours under a normal pressure condition at 150° C. to obtain 144 g of a food material.

Comparison Example 3

Test Example 1 was repeated except the distillation in the third process was carried out for three hours under a normal pressure condition at 150° C., instead of three hours under reduced pressure of 1 KPa at 80° C., to obtain 177 g of a food material.

Analyses and Evaluations

The food materials thus obtained were analyzed and evaluated as below for residual hexane, sesaminol triglucoside, water content, color, flavor and taste. The results are shown in Tables 1 and 2.

For the analyses of hexane, each of the food materials 3 g was dispersed in a liquid mixture with 30 ml of 2,2,4-trimethylpentane and 20 ml of distilled water. This dispersion was distilled to distill away 20 ml of the mixed liquid of 2,2,4-trimethylpentane and hexane. After n-dodecane 1000 ppm was added to this mixed liquid as internal standard, 2,2,4-trimethylpentane was added to provide 25 ml of sample for analysis. These samples were analyzed for residual hexane by gas chromatography as described below.

Stationary phase: TC-1 produced by Gasukuro, Inc.
Column diameter: 0.53 mm
Column length: 30 m
Carrier gas: Nitrogen
Carrier flow rate: 6 ml/minute
Inlet temperature: 150° C.
Detector temperature: 200° C.
Column temperature: Held at 50° C. for 8 minutes, raised to 200° C. at rate of 10° C./minute, held at 200° C. for 2 minutes
Detector: FID
Standard liquid for detection: Diluted to specified concentration 2-methyl pentane, 3-methylpentane, n-hexane and methylcyclopentane as hexane component and n-dodecane as internal standard with 2,2,4-trimethylpentane. The amount of residual hexane is expressed as the total of 2-methylpentane, 3-methylpentane, n-hexane and methylcyclopentane.

If the measured value was less than 5 ppm which is the limit of reliability, it was recorded as "None" in Tables 1 and 2.

For the analyses of sesaminol triglucoside, each food material 5 g was taken in a container with a stirrer and stirred for 12 hours at room temperature with 80% aqueous solution of ethanol 250 ml. Undissolved components were separated by centrifugal separation to collect the supernatant. This supernatant was filtered by a membrane filter and the filtered liquid was used as sample for analyzing for sesaminol triglucoside. These samples were analyzed for sesaminol triglucoside by high-speed liquid chromatography as described below. The standard sample was obtained by the method described in Phytochemistry Vol. 35, 773–776 (1994).

Stationary phase: Develosil ODS-10 produced by Nomura Chemical Co., Ltd.
Column diameter: 6 mm
Column length: 250 mm
Solvent for development: Linear gradient of 40 minutes from 30% aqueous solution of methyl alcohol to 80% aqueous solution of methyl alcohol
Flow rate of solvent for development: 1 ml/minute
Detector: UV (290 nm)

For the analysis of color, Chroma Meter II Reflectance (product of Minolta Camera Co., Ltd.) was used to measure the L-value, the a-value and the b-value. Measurements were taken three times and the average was recorded.

Flavor and taste (feeling in the mouth) were tested for each sample by a 5-point method (that is, the better the result, the higher the points) by a panel of 50 testers consisting of 6 men and 6 women at ages 20–29, 7 men and 7 women at ages 30–39, 5 men and 5 women at ages 40–49, 4 men and 4 women at ages 50–59 and 3 men and 3 women at ages 60–69. The average values and standard deviations are shown.

TABLE 1

|  | Test Examples | | | |
| --- | --- | --- | --- | --- |
|  | 1 | 2 | 3 | 4 |
| First Process |  |  |  |  |
| Extraction temperature (°C.) | 50 | 50 | 50 | 100 |
| Solvent content (%) | 1.5 | 1.5 | 1.5 | 4.3 |
| Second Process |  |  |  |  |
| Water added (part) | 40 | 40 | 60 | 90 |
| Third Process |  |  |  |  |

TABLE 1-continued

|  | Test Examples | | | |
|---|---|---|---|---|
|  | 1 | 2 | 3 | 4 |
| Distillation temperature (°C.) | 80*[1] | 80 | 80*[1] | 110 |
| Distillation time (hour) | 5 | 7 | 5 | 4 |
| Hexane (ppm) | None | None | None | None |
| Sesaminol triglucoside (mg/g) | 4.3 | 3.9 | 4.2 | 3.8 |
| Water (%) | 1.2 | 2.5 | 1.2 | 0 |
| Color | | | | |
| L-value | 89.31 | 87.54 | 88.42 | 86.28 |
| a-value | −0.90 | −0.48 | −0.89 | −0.27 |
| b-value | 7.69 | 8.01 | 7.73 | 8.04 |
| Flavor | | | | |
| Average (**) | 4.98 | 4.94 | 4.96 | 4.94 |
| Standard deviation | 0.14 | 0.24 | 0.20 | 0.24 |
| Taste | | | | |
| Average (**) | 4.98 | 4.98 | 4.98 | 4.96 |
| Standard deviation | 0.14 | 0.14 | 0.14 | 0.20 |
| General feeling in mouth | | | | |
| Average (**) | 4.98 | 4.96 | 4.98 | 4.96 |
| Standard deviation | 0.14 | 0.20 | 0.14 | 0.20 |

*[1]: Distillation was carried out at 1 KPa.
**: Each test example result is significant with reliability of less than 1% with respect to Comparison Example 1 in Table 2.

TABLE 2

|  | Comparison Examples | | |
|---|---|---|---|
|  | 1 | 2 | 3 |
| First Process | | | |
| Extraction temperature (°C.) | 50 | 50 | 50 |
| Solvent content (%) | 1.5 | 20 | 1.5 |
| Second Process | | | |
| Water added (part) | 0 | 40 | 40 |
| Third Process | | | |
| Distillation temperature (°C.) | *2 | *2 | 150 |
| Distillation time (hour) | *2 | *2 | 3 |
| Hexane (ppm) | None | None | None |
| Sesaminol triglucoside (mg/g) | 1.4 | 1.6 | 2.3 |
| Water (%) | 0 | 0 | 0 |
| Color | | | |
| L-value | 69.88 | 73.26 | 75.24 |
| a-value | 5.04 | 4.32 | 2.91 |
| b-value | 28.31 | 26.10 | 24.00 |
| Flavor | | | |
| Average (**) | 1.74 | 1.20 | 2.16 |
| Standard deviation | 0.52 | 0.40 | 0.54 |
| Taste | | | |
| Average (**) | 1.62 | 2.18 | 2.34 |
| Standard deviation | 0.52 | 0.52 | 0.68 |
| General feeling in mouth | | | |
| Average (**) | 1.52 | 1.70 | 2.52 |
| Standard deviation | 1.54 | 0.50 | 0.50 |

*2: After the distillation of solvent for 5 hours at 1 KPa and 80° C., another distillation process was carried out for 3 hours at normal pressure and 150° C.

Part 2 (Examples wherein aqueous solution of ethyl alcohol is used in the second process)

Following sample food materials were prepared, tested and analyzed as in Part 1. The results of the tests are shown in Table 3.

Test Examples 5 and 6

Instead of the 80 g of water in the second process in Test Example 1, use was made of 144 g of aqueous solution of ethyl alcohol with weight ratio of water/ethyl alcohol=80/64 in Test Example 5 and 176 g of aqueous solution of ethyl alcohol with weight ratio of water/ethyl alcohol=80/96 in Test Example 6 to obtain 11 g and 180 g of respective food materials.

Part 3 (Examples wherein buffer water is used in the second process)

Following sample food materials were prepared, tested and analyzed as in Part 1. The results of the tests are shown in Table 4.

Test Examples 7 and 8

Instead of the 80 g of water in the second process in Test Example 1, use was made of 80 g of buffer water of pH 7.1 with potassium dihydrogen phosphate-sodium hydroxide buffer in Test Example 7 and 160 g of aqueous solution of ethyl alcohol with weight ratio of 80/80 between buffer of pH 8.8 with glycine-sodium chloride-sodium hydroxide buffer and ethyl alcohol in Test Example 8 to obtain 182 g and 181 g of respective food materials.

TABLE 3

|  | Test Examples | |
|---|---|---|
|  | 5 | 6 |
| First Process | | |
| Extraction temperature (°C.) | 50 | 50 |
| Solvent content (%) | 1.5 | 1.5 |
| Second Process | | |
| Water added (part) | 40 | 40 |
| Ratio of ethyl alcohol (part) | 80 | 120 |
| Third Process | | |
| Distillation temperature (°C.) | 80*[1] | 80*[1] |
| Distillation time (hour) | 5 | 5 |
| Hexane (ppm) | None | None |
| Sesaminol triglucoside (mg/g) | 4.5 | 4.5 |
| Water (%) | 1.1 | 1.2 |
| Color | | |
| L-value | 91.02 | 91.58 |
| a-value | −0.90 | −0.91 |
| b-value | 7.21 | 7.18 |
| Flavor | | |
| Average (**) | 4.98 | 4.96 |
| Standard deviation | 0.14 | 0.20 |
| Taste | | |
| Average (**) | 4.96 | 4.98 |
| Standard deviation | 0.20 | 0.14 |
| General feeling in mouth | | |
| Average (**) | 5.00 | 5.00 |
| Standard deviation | 0. | 0. |

Ratio of ethyl alcohol is the added amount for 100 weight part of water.
*[1]: Distillation was carried out at 1 KPa.
**: Each test example result is significant with reliability of less than 1% with respect to Comparison Example 1 in Table 2.

TABLE 4

|  | Test Examples | |
|---|---|---|
|  | 7 | 8 |
| First Process | | |
| Extraction temperature (°C.) | 50 | 50 |
| Solvent content (%) | 1.5 | 1.5 |
| Second Process | | |
| Water added (part) | 40 | 40 |
| Ratio of ethyl alcohol (part) | 0 | 100 |
| pH of buffer | 7.1 | 8.8 |
| Third Process | | |
| Distillation temperature (°C.) | 80*[1] | 80*[1] |
| Distillation time (hour) | 5 | 5 |
| Hexane (ppm) | None | None |
| Sesaminol triglucoside (mg/g) | 4.6 | 4.7 |
| Water (%) | 1.2 | 1.1 |
| Color | | |
| L-value | 91.88 | 92.72 |
| a-value | −0.92 | −1.10 |
| b-value | 7.06 | 7.02 |
| Flavor | | |
| Average (**) | 5.00 | 5.00 |
| Standard deviation | 0. | 0. |
| Taste | | |
| Average (**) | 4.98 | 4.98 |
| Standard deviation | 0.14 | 0.14 |
| General feeling in mouth | | |
| Average (**) | 4.98 | 5.00 |
| Standard deviation | 0.14 | 0. |

*[1]: Distillation was carried out at 1 KPa.

The results of these tests clearly show that new food materials according to this invention contain substantially no extraction solvent, contain sesaminol triglucoside derived from sesame seeds at high concentrations and have superior color, flavor and taste.

What is claimed is:

1. A method of producing a food material; said method comprising:

a first process of subjecting dehulled sesame seeds to an extraction process at an extraction temperature below 120° C. with aliphatic hydrocarbon as extraction solvent to obtain a solution and removing said solution to obtain a solid which contains said extraction solvent by less than 10 weight %;

a second process of adding water to said solid to thereby obtain a water-containing object; and a third process of removing remainder of said extraction solvent from said water-containing object by distillation at a distillation temperature of 20–120° C., wherein a food material containing sesaminol triglucoside by at least 3.0 mg per 1 g of dry component and substantially not containing said extraction solvent is obtained.

2. The method of claim 1 wherein ethyl alcohol is also added to said solid in said second process at a rate of 50–200 weight parts per 100 weight parts of said water.

3. The method of claim 1 wherein said water which is added in said second process is a buffer water with pH 7–9.

4. The method of claim 2 wherein said water which is added in said second process is a buffer water with pH 7–9.

* * * * *